United States Patent [19]

Goetz et al.

[11] 4,390,546

[45] Jun. 28, 1983

[54] ANTIPARASITIC MACROLIDE FROM A STRAIN OF *STREPTOMYCES HYGROSCOPICUS*

[75] Inventors: Michael A. Goetz, North Plainfield; Pamela A. McCormick, Willingboro; Richard L. Monaghan, Somerset, all of N.J.

[73] Assignee: Merck & Co., Inc., Rahway, N.J.

[21] Appl. No.: 327,838

[22] Filed: Dec. 7, 1981

[51] Int. Cl.$^3$ .................. C07D 313/00; A61K 31/365
[52] U.S. Cl. .................................... 424/279; 542/416; 435/118
[58] Field of Search .......................... 542/416; 424/279

[56] References Cited

PUBLICATIONS

Derwent Abstract 3189-Abstracting British Patent 850,325.
*Chemical Abstracts,* 56 14091d (1962).
Gottlieb-"Flavensomycin" appearing in Antibiotics I, pp. 617-620 (1967).
Canonica et al., (I) *Tetrahedron Letters* 16, pp.537-543 (1961).
Canonica et al., (II) *Tetrahedron Letters* 26, pp. 3031-3034 (1966).
Box et al., *Applied Microbiology* 26, pp. 699-704 (1973).
Grove et al. *Journal of the Chemical Society,* Perkin I, pp. 2441-2443 (1967).

*Primary Examiner*—Jane T. Fan
*Attorney, Agent, or Firm*—David L. Rose; Mario A. Monaco

[57] ABSTRACT

There is disclosed a macrolide isolated from the fermentation broth of a microorganism identified as MA-5285 which morphological analysis reveals to be a strain of *Streptomyces hygroscopicus.* The compound's structure is presented based upon analytical studies. The compound has insecticidal and antiparasitic activity.

5 Claims, 1 Drawing Figure

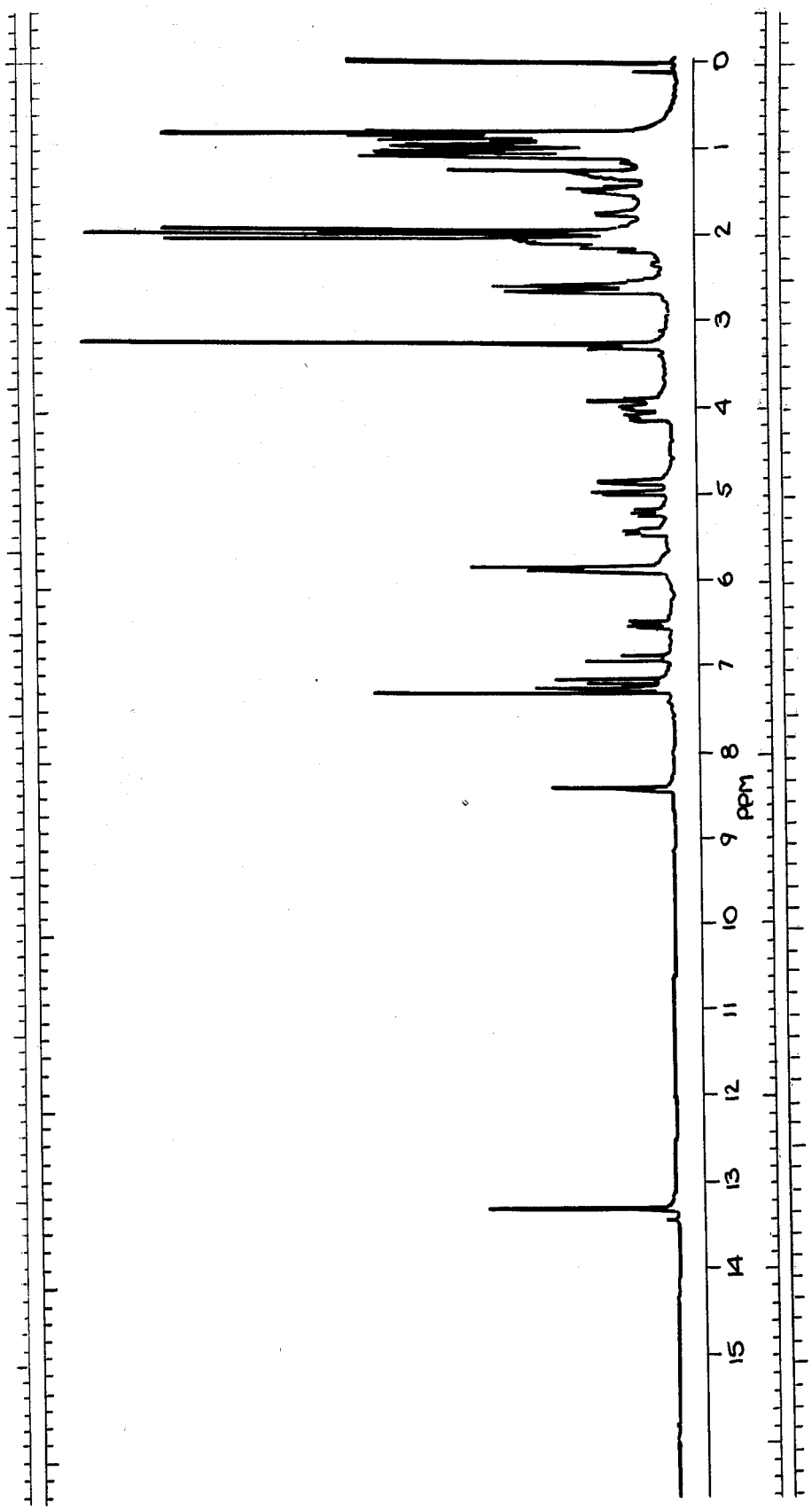

ANTIPARASITIC MACROLIDE FROM A STRAIN OF *STREPTOMYCES HYGROSCOPICUS*

SUMMARY OF THE INVENTION

This invention is concerned with a novel chemical compound. In particular, it is concerned with a novel macrocyclic lactone which is produced by the fermentation of a nutrient medium with a strain of the microorganism *Streptomyces hygroscopicus* MA-5285. Thus, it is an object of this invention to provide for such novel compound, and a method for preparing such product microbiologically. It is a further object of this invention to provide for the recovery and purification of such compound from the fermentation broth. This substance has antiparasitic and insecticidal activity, in particular antitapeworm, antigiardiasis and antitrichomonas activity, and it is, thus, an additional object of this invention to provide novel antiparasitic and insecticidal compositions containing the disclosed compound. Further objects of this invention will become apparent from the following description of this invention.

DESCRIPTION OF THE INVENTION

In accordance with this invention, a novel substance is described, which is prepared by growing under controlled conditions, a previously undescribed strain of microorganism. A single novel compound is produced by *Streptomyces hygroscopicus* MA-5285. The compound is obtained by fermentation and recovered in substantially pure form as described herein.

Based on taxonomic studies, the microorganism capable of producing these compounds are of a new strain of the microorganism *Streptomyces hygroscopicus*. One such culture, isolted from soil, is designated MA-5285 in the culture collection of Merck & Co., Inc., Rahway, New Jersey. A sample of this culture, capable of producing the herein described compound, has been deposited, without restriction as to availability, in the permanent culture collection of the American Type Culture Collection at 12301 Parklawn Drive, Rockville, Maryland 20852, and has been assigned the accession number ATCC 31955.

The morphological and cultural characteristics of *Streptomyces hygroscopicus* MA-5285 are set forth below:

CULTURAL CHARACTERISTIC OF:

*Streptomyces hygroscopicus* MA-5285-ATCC 31955 (V-vegetative growth; A=aerial mycelium; SP=soluble pigment)

Morphology: Sporophores form compact spirals, clustering along aerial mycelia. The coils of spores are hygroscopic, coalescing to form black moist droplets. Spore surface is predominantly rugose to warty with some smooth surfaced spores (transition electron microscopy).

Oatmeal agar (ISP Medium 3)
  V: Reverse—tan
  A: Dark gray edged with white. As culture ages, the entire gray spore mass becomes black, moist looking and soft.
  SP: None Czapek Dox agar (sucrose nitrate agar)
  V: Reverse—pinkish grayed cream
  A: Light and dark gray mixed with white
  SP: Very light gray Egg albumin agar
  V: Reverse—grayish cream
  A: Light gray, moderate. As culture ages, moist black areas appear.
  SP: None Glycerol asparagine agar (ISP Medium 5)
  V: Reverse—Dark brown
  A: Medium gray edged with white
  SP: Light pinkish gray Inorganic salts-starch agar (ISP Medium 4)
  V: Reverse—tan
  A: Light gray edged with dark gray. As culture ages, moist black areas appear.
  SP: None Yeast extract-malt extract agar (ISP Medium 2)
  V: Reverse—brown
  A: Dark gray edged with white. As culture ages, entire gray spore mass becomes black, moist looking and soft.
  SP: Light brown Peptone-iron-yeast extract agar
  V: Cream-colored
  A: Sparse, whitish
  SP: None Tyrosine agar:
  V: Brown edged with dark brown
  A: Grayish-white, moderate
  SP: Light brown

Carbon Utilization

Pridham-Gottlieb basal medium+1% carbon source; +=growth; ±=growth poor or questionable; −=no growth as compared to negative control (no carbon source)

| | |
|---|---|
| Glucose | + |
| Arabinose | ± |
| Cellulose | − |
| Fructose | ± |
| Inositol | ± |
| Lactose | ± |
| Maltose | ± |
| Mannitol | ± |
| Mannose | ± |
| Raffinose | ± |
| Rhamnose | ± |
| Sucrose | − |
| Xylose | ± |

Temperature range (Yeast extract-dextrose+salts agar)
28° C.—Good vegetative growth; good aerial mycelia and sporulation
37° C.—Good vegetative growth; sparse aerial mycelia
50° C.—No growth
Oxygen requirements (Stab culture in yeast extract-dextrose+salts agar)

Aerobic

All readings taken after three weeks at 28° C. unless noted otherwise. pH of all media approximately neutral (6.8-7.2)

A careful comparison of the foregoing data with published descriptions, including Bergey's *Manual of Determinative Bacteriology* 8th ed (1974); Waksman, *The Actinomycetes* Vol. II (1961); International Journal of Systematic Bacteriology 18, 68–189, 279–392 (1968); 19, 391–512 (1969); 22, 265–394 (1972); shows a close correlation between the description of a bacterium identified as *Streptomyces hygroscopicus* and the morphological and cultural characteristics of MA-5285. It is therefore determined that MA-5285 is a strain of the known species *Streptomyces hygroscopicus*.

The above description is illustrative of a strain of *Streptomyces hygroscopicus* MA-5285 which can be employed in the production of the instant compound. However, the present invention also embraces mutants of the above described microorganism. For example, those mutants which are obtained by natural selection of those produced by mutating agents including ionizing radiation such as ultraviolet irradiation, or chemical mutagens such as nitrosoguanidine or the like treatments are also included within the ambit of this invention.

The instant compound is produced during the aerobic fermentation of suitable aqueous nutrient media under conditions described hereinafter, with a producing strain of *Streptomyces hygroscopicus* MA-5285. Aqueous media such as those used for the production of many antibiotic substances are suitable for use in this process for the production of this macrocyclic compound.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources may be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Streptomyces hygroscopicus* MA-5285 in the production of the instant compound. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like. For the best production of the instant compound, the addition of calcium carbonate to the production medium is most preferred.

It should be noted that the media described hereinbelow and in the Examples are merely illustrative of the wide variety of media, which may be employed, and are not intended to be limitative.

The following are Examples of media suitable for growing strains of *Streptomyces hygroscopicus* MA-5285.

| Medium A | |
|---|---|
| Dextrose | 1.0 g. |
| Soluble starch | 10.0 g |
| Beef extract | 3.0 g. |
| Yeast autolysate (As ardamine pH available from Yeast Products, Inc., Clifton, N.J.) | 5.0 g. |
| NZ Amine-E (caesin hydrolysate-available from Humko-Sheffield-Memphis, Tenn.) | 5.0 g. |
| $MgSO_4.7H_2O$ | 0.05 g. |
| Phosphate Buffer | 2.0 ml |
| $CaCO_3$ | 0.5 g. |
| Distilled water | 1000 ml. |
| pH 7.0–7.2 | |
| Phosphate Buffer | |
| $KH_2PO_4$ | 91.0 g |
| $Na_2HPO_4$ | 95.0 g |
| Distilled water | 1000 ml |
| pH 7.0 | |
| Medium B | |
| Tomato paste | 20.0 g. |
| Primary yeast | 10.0 g. |
| Dextrin (CPC starch) | 20.0 g. |
| $CoCl_2.6H_2O$ | 0.005 g. |
| Distilled water | 1000 ml. |
| pH 7.2–7.4 | |
| Medium C | |
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g. |
| $FeSO_4.2H_2O$ | 0.01 g. |
| Polyglycol P2000 (Polypropylene glycol mw 2000) | 2.5 mg. |
| Distilled water | 1000 ml. |
| pH 6.5 | |
| Medium D | |
| Lactose | 20.0 g. |
| Distillers solubles | 15.0 g. |
| Autolyzed yeast (Ardamine pH) | 5.0 g. |
| Distilled water | q.s. to 1000 ml. |
| pH 7.0 | |
| Medium E | |
| Tomato paste | 40.0 g. |
| Oat flour | 10.0 g. |
| Distilled water | 1000 ml. |
| pH 7.0 | |
| Medium F | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH 6.7 | |
| Medium G | |
| Dextrose | 10.0 g |
| Asparagine | 1.0 g |
| $K_2HPO_4$ | 0.1 g |
| $MgSO_4.7H_2O$ | 0.5 g |
| Yeast Extract | 0.5 g |
| Oat Flour | 10.0 g |
| $CaCO_3$ | 3.0 g |
| Trace Element Mix | 10.0 ml |
| Distilled water | 1000 ml |
| Adjust pH to 7.2 | |
| Trace Element Mix | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |

| -continued | |
|---|---|
| $(NH_4)_6MO_4O_{24} \cdot 6H_2O$ | 19 mg |
| $ZnSO_4 \cdot 7H_2O$ | 200 mg |
| Distilled water | 1000 ml |
| Medium H | |
| Medium G | 1000 ml |
| Oat Flour | 10 g |
| pH 7.2 | |

The fermentation employing *Streptomyces hygroscopicus* MA-5285 can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Streptomyces hygroscopicus* MA-5285 loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces hygroscopicus* MA-5285. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 RPM and about 2 to 20 cubic feet per minute (CFM) of air.

The novel compound of this invention is found primarily in the mycelium on termination of the *Streptomyces hygroscopicus* MA-5285 fermentation and may be removed and separated therefrom as described below.

The separation of the novel compound from the whole fermentation broth and the recovery of said compounds is carried out by solvent extraction and application of chromatographic fractionations with various chromatographic techniques and solvent systems.

The instant compound has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the non-polar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as others known to those skilled in the art, will afford purified compositions containing the instant compound. The presence of the desired compound is determined by analyzing the various chromatographic fractions for biological activity against tapeworm or against *Giardia lamblia*, or physico-chemical characteristics. The structures of the instant compound has been determined by detailed analysis of the various spectral characteristics of the compounds, in particular their nuclear magnetic resonance, mass, ultraviolet and infrared spectra. The compound has a molecular formula of $C_{43}H_{63}NO_{12}$ and a molecular weight of 785.

In the mass spectral analysis of the instant compound no molecular ion was observed, however, the following ions and their proposed emperical formulas are given below ($M^+$ is the molecular ion).

| Peak | Molecular Weight | Emperical Formula | Derivative |
|---|---|---|---|
| $M^+$app | 574.3879 | $C_{34}H_{54}O_7$ | $M^+$-fumaric acid |
| | 556.3760 | $C_{34}H_{52}O_6$ | $M^+$app-water |
| | 538.3654 | $C_{34}H_{50}O_5$ | $M^+$app-2 water |
| | 542.3563 | $C_{33}H_{50}O_6$ | $M^+$app-methanol |
| | 404 | $C_{24}H_{76}O_5$ | |
| | 318.2153 | $C_{20}H_{30}O_3$ | |
| | 234.1617 | $C_{15}H_{22}O_2$ | |
| | 211.0475 | $C_9H_9NO_5$ | |

The 300 MHz proton nuclear magnetic resonance spectrum of this compound, carried out in deuterated chloroform with tetramethyl silane as an internal standard is shown in the attached FIGURE.

In addition, a $^{13}C$ nuclear magnetic resonance spectrum at 75.1 MHz (15 mg of the compound in 0.35 ml of $CDCl_3$ at 20° C.) reveals the following chemical shifts in ppm downfield relative to tetramethyl silane as an internal standard: 5.0, 7.0, 9.8, 10.8, 13.8, 15.3, 17.6, 20.2, 21.6, 25.4, 25.9, 32.3, 34.4, 35.5, 36.8, 38.0, 39.9, 41.3, 41.7, 55.7, 70.5, 71.3, 73.3, 76.3, 81.5, 82.8, 99.6, 115.3, 122.6, 125.6, 127.7, 132.9, 133.7, 133.8, 134.9, 143.1, 145.2, 147.2, 164.3, 164.5, 172.6, 176.1, and 198.5.

Based on these experimental data, the instant compound is believed to have the following structural formula:

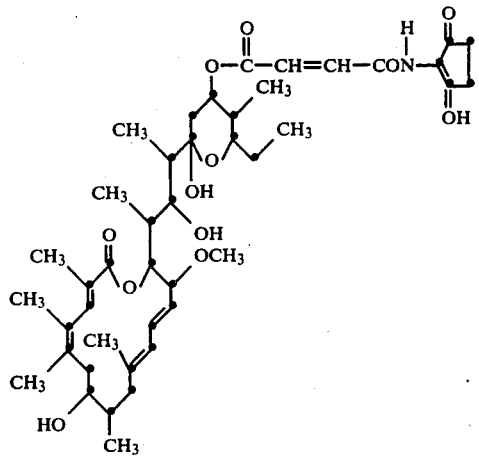

The novel compound of this invention has significant parasiticidal activity. In particular the compound has significant activity against tapeworms. The compound is also of value as an insecticide. For example, the compound is effective against the larvae of *Lucilia cuprina*. In addition, the compound has anticoccidial and antigiardial (*Giardia lamblia*) activity.

Giardiasis is caused by the parasite *Giardia lamblia* and is considered to be the most common intestinal parasitic infection in the United States and in some other countries. The parasite is cosmopolitan and can strike anyone regardless of their area of residence or social position. Children, however, are very often victims of the parasite. The parasite causes a variety of intestinal symptoms, such as prolonged diarrhea, abdominal cramps, stomach pain, severe weight loss, fatigue, nausea, and flatulence. While the symptoms can be severe, the disease is generally not fatal. Giardiasis can also cause malabsorption of nutrients and even retarded growth. Furthermore, giardiasis can mimic the symptoms of other conditions such as ulcers, and gall bladder attacks. If misdiagnosed, a patient may have a series of costly, needless tests and even surgery, which further delays the actual treatment of the giardiasis.

The infection is generally treated with one of three drugs: Atabrine, Flagyl or furazolidone. However each of these drugs is known to cause serious adverse side effects. The search for a safe effective treatment of giardiasis thus is continuing. See L. K. Altman, *The New York Times*, pg C-1, 10 June 1980.

Trichomonas is an infection of the lower genitourinary tract, which may be induced in men and women by the protozoan parasite *Trichomonas vaginalis*. The infection may produce a few symptoms of such extreme discomfort and morbidity that intervention from a gynecologist or a urologist is necessary. The disease is of cosmopolitan distribution and apparently 10–25% of sexually mature females and 25–80% of their consorts are involved (E. A. Steck, The Chemotherapy of Protozoa Diaseases, Vol. II, Section 3, 17-1, 1971). Trichomoniasis is presently treated with Flagyl (metronidazole), which, as noted above has serious side effects associated with its administration.

The compound is particularly active against tapeworms, a form of cestode parasites, which infect man and animals. The tapeworm is a common parasite which, although often symptomless, can lead to various gastrointestinal and other disorders. Tapeworms such as *Hymenolepis diminuta*, *Hymenolepis nana*, *Taenia saginata*, *Taenia solium* and *Diphyllobothrium latum* are commonly found in such infections.

When the compound of this invention is administered for the treatment of tapeworms, oral administration is preferred.

The active compound of the present invention, when used to treat the above disorders, is orally administered, for example, with an inert diluent, an organic solvent or with an assimilable edible carrier, or they may be enclosed in hard or soft gelatin capsules, or they may be compressed into tablets, or they may be incorporated directly with the food of the diet. For oral therapeutic administration, the active compound of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pill, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amount employed.

When used in the above formulation, the instant compound is employed at dosages sufficient to treat tapeworm infections. The dosages may be given a single daily dose or in divided dosages throughout the day. The specific dose given to a patient will vary with the severity of the condition, and the weight of the patient. As such, dosages of from about 1 to 25 mg/kg/day have been found to be effective. Such doses may be divided to provide for up to 4 administrations per day. The treatment may be carried out over several days to ensure that the parasite is completely destroyed. Generally, treatment period of from 1 to 21 days are adequate.

The following examples are being provided in order that the instant invention may be more fully understood. Such examples are not to be construed as being limitative of the invention.

EXAMPLE 1

Fermentation

A lyophilized tube of *Streptomyces hygroscopicus* MA-5285 is aseptically transferred into 54 ml of Medium A in a 250 ml baffled Erlenmeyer flask and incubated at 28° C. for 2 days on a rotary shaking machine at 220 rpm in a 2 inch radius circular orbit. At the end of this time approximately 40 ml of the contents of the flask are used to inoculate 300 ml of Medium F in a 2 l unbaffled Erlenmeyer flask, which is then incubated for 4 days at 28° C. on a rotary shaking machine at 150 rpm in a 2 inch radius circular orbit.

EXAMPLE 2

The contents of a lyophilized tube of MA-5285 is transferred aseptically to a 250 ml baffled Erlenmeyer flask containing 54 ml of Medium A. The inoculated flask is incubated for 4 days at 28° C. on a rotary shaking machine at a speed of 220 rpm on a 2 inch radius circular orbit. At the end of this time, 2.0 ml of this material is used to inoculate a 250 ml Erlenmeyer flask containing 44 ml of either Medium B, G or H. These inoculated flasks are incubated at 28° C. for 4 days on a rotary shaker at a speed of 220 rpm in a 2 inch radius circular orbit.

EXAMPLE 3

Extraction and Isolation

One liter of the whole broth from Example 1 is extracted twice and one liter of ethyl acetate; the layers are separated.

After evaporation in vacuo of the organic layer, the residue (750 mg) is taken up in 10 ml of methanol-methylene chloride (20:1) and fractionated on a 4.3 liter Sephadex LH-20 column and eluted with methanol. The column is eluted taking 300 fractions of 20 ml each.

Tapeworm assay of the resulting fractions indicates activity to be restricted to one single zone eluted between 0.79 and 0.84 column volumes.

The tapeworm-active mixture is then evaporated, in vacuo, to dryness (solid residue: 65 mg), redissolved in 2 ml of methylene chloride-methanol (93:7) and further fractionated by silica gel column chromatography using E. Merck Lobar silica gel column, 2.5 cm in diameter and 31 cm. long, eluting with a methylene chloride-methanol, gradient from 93:7 to 80:20. The column is eluted taking 300 fractions of 6 ml each.

Tapeworm assay of the resulting fractions indicates the activity to be restricted to one zone eluted between 1.2 and 1.6 column volumes.

The active mixture thus obtained is evaporated in vacuo (solid residue weighs 2.5 mg), redissolved in 0.4 ml 75% methanol and further fractionated by reversed-phase HPLC (Whatman Magnum 9 ODS-3 column eluted with $CH_3CN$-0.01 M, pH 3, ammonium phosphate, gradient from 40:60 to 95:5).

Tapeworm assay revealed that activity is found in one zone, eluted between 6.5 and 7.5 column volumes (weight: 1.5 mg approximately).

Final purification of the main, active component to eliminate trace impurities, is achieved by silica gel HPLC (Whatman 25 cm long×4 mm ID silica gel column; chloroform-acetic acid 99:1). The pure compound weight obtained is 1.4 mg.

EXAMPLE 4

The assay used to determine the presence of the tapeworm active fractions in Example 3 is as set forth below.

Rats are infected with mature *Hymenolipsis diminuta* and the infections are allowed to mature. The rats are then administered and compound being tested by gavage. After from 2 to 6 days the rats are sacrificed and necropsied. The small intestine is examined for tapeworms.

EXAMPLE 5

In each well of a multiwell plate is placed 1.4 ml of Diamond's TPS medium (See Table I) at pH 7.05, 10% by volume of heat-inactivated fetal bovine serum, and 1% by volume of an antibiotic-antimycotic solution (see Table II). A suspension of *Giardia lamblia* is centrifuged at 2,500 xg for 6 minutes. The pelleted cells are resuspended in a small volume of Diamond's medium, the cells are counted and each well inoculated with approximately $10^6$ organisms. The fractions obtained during the isolation procedure are evaporated to dryness and the residue dissolved in dimethylsulfoxide. The wells are then inoculated with various fractions of the compound to determine its presence. The plates are incubated for 24 hours at 37° C. in an anaerobic Gas Pak jar. After 24 hours of incubation, each well is mixed and counted for viable organisms using a hemacytometer. The percentage of survival is determined by comparing the treated wells to controls treated with dimethylsulfoxide. The presence of the compound in a particular fraction is noted when the well analysis indicates that a substantial portion of the Giardia have been killed.

TABLE I

| Composition of Diamond's TPS Medium | |
| --- | --- |
| Ingredients | Amounts |
| Trypticase (BBL) | 1.00 g. |
| Panmede, liver digest P&B | 2.00 g. |
| Glucose | 0.50 g. |
| L-cysteine monohydrochloride | 0.10 g. |
| Ascorbic acid | 0.02 g. |
| Sodium chloride | 0.50 g. |
| Potassium phosphate. monobasic | 0.06 g. |
| Potassium phosphate dibasic, anhydrous | 0.10 g. |
| Water, glass distilled | 87.50 ml. |
| pH adjusted to 7.0 with 1N NaOH | |

TABLE II

| Antibiotic Antimycotic Solution (100X) | |
| --- | --- |
| Ingredients | Amounts |
| Penicillin | 10,000 units |
| Streptomycin | 10,000 mcg |
| Fungizone ® | 25 mcg |

Prepared in normal saline

What is claimed is:
1. A compound having the formula:

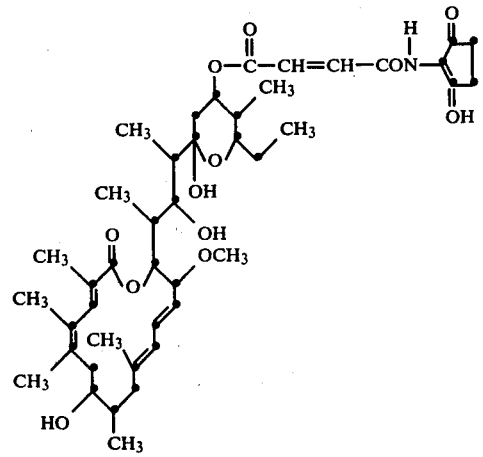

2. A composition useful for the prevention and treatment of parasitic infections which comprises an inert carrier having the compound of claim 1 incorporated therein.

3. The composition of claim 2 wherein the parasitic infection is a tapeworm.

4. A method for the prevention and treatment of parasitic infections which comprises administering to an animal infected with parasites, an effective amount of the compound of claim 1.

5. The composition of claim 4 wherein the parasitic infection is a tapeworm.

* * * * *

UNITED STATES PATENT AND TRADEMARK OFFICE
CERTIFICATE OF CORRECTION

PATENT NO. : 4,390,546

DATED : 6-28-83

INVENTOR(S) : MICHAEL A. GOETZ et al

It is certified that error appears in the above—identified patent and that said Letters Patent is hereby corrected as shown below:

Column 7 lines 1-7 and Column 10 lines 50-55 far right portion of the structural formula should be:

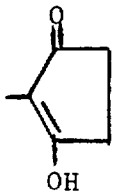

Column 9 line 22 should read --twice with one liter--

Signed and Sealed this

Twenty-seventh Day of September 1983

[SEAL]

Attest:

GERALD J. MOSSINGHOFF

Attesting Officer    Commissioner of Patents and Trademarks